(12) United States Patent
Yang et al.

(10) Patent No.: US 10,308,563 B2
(45) Date of Patent: Jun. 4, 2019

(54) PROCESS FOR PRODUCING ETHYLENE OLIGOMERS

(71) Applicant: HANWHA TOTAL PETROCHEMICAL CO., LTD., Seosan-si (KR)

(72) Inventors: Chun Byung Yang, Seosan-si (KR); Eun Il Kim, Seosan-si (KR)

(73) Assignee: Hanwha Total Petrochemical Co., Ltd., Seosan-si (KR)

( * ) Notice: Subject to any disclaimer, the term of this patent is extended or adjusted under 35 U.S.C. 154(b) by 20 days.

(21) Appl. No.: 15/836,355

(22) Filed: Dec. 8, 2017

(65) Prior Publication Data

US 2018/0170827 A1 Jun. 21, 2018

(30) Foreign Application Priority Data

Dec. 15, 2016 (KR) .................. 10-2016-0171460

(51) Int. Cl.

| | |
|---|---|
| *B01D 3/06* | (2006.01) |
| *B01D 3/14* | (2006.01) |
| *C07C 2/32* | (2006.01) |
| *C08F 4/32* | (2006.01) |
| *C01G 25/04* | (2006.01) |
| *C07C 11/02* | (2006.01) |
| *G01N 30/02* | (2006.01) |
| *C07C 11/107* | (2006.01) |
| *C08F 110/02* | (2006.01) |

(52) U.S. Cl.
CPC .................. *C07C 2/32* (2013.01); *B01D 3/06* (2013.01); *B01D 3/14* (2013.01); *C07C 11/02* (2013.01);

(Continued)

(58) Field of Classification Search
None
See application file for complete search history.

(56) References Cited

U.S. PATENT DOCUMENTS

| | | |
|---|---|---|
| 3,676,523 A | 7/1972 | Mason |
| 3,906,053 A | 9/1975 | Lanier |
| | (Continued) | |

FOREIGN PATENT DOCUMENTS

| | | |
|---|---|---|
| DE | 1443927 U | 8/1938 |
| EP | 0177999 B1 | 1/1989 |
| | (Continued) | |

*Primary Examiner* — In Suk C Bullock
*Assistant Examiner* — Ali Z Fadhel
(74) *Attorney, Agent, or Firm* — Harness, Dickey & Pierce, P.L.C.

(57) ABSTRACT

The present disclosure relates to a process for producing ethylene oligomers and more particularly, to a process for oligomerizing ethylene by recycling butene, hexene, and octene in an ethylene oligomerization reaction with a catalyst system including a transition metal or transition metal precursor, a ligand with a backbone structure expressed by the following Chemical Formula 1, and a co-catalyst. [Chemical Formula 1] $R^1$—O—Y—O—$R^2$ or $R^1$—OC(=O)—Y—C(=O)O$R^2$ Herein, $R^1$, $R^2$ are each independently hydrocarbyl, substituted hydrocarbyl, heterohydrocarbyl, or substituted heterohydrocarbyl, and Y represents a group connecting O or C(=O)O and is hydrocarbyl, substituted hydrocarbyl, hetero hydrocarbyl, or substituted heterohydrocarbyl. According to the oligomerization method of the present disclosure, in the distribution of the produced α-olefins, C10"-C12" α-olefins care highly distributed, the produced α-olefins have a remarkably high purity.

11 Claims, 1 Drawing Sheet

(52) U.S. Cl.
CPC .............. *C08F 4/32* (2013.01); *C08F 110/02* (2013.01); *C01G 25/04* (2013.01); *C07C 2531/22* (2013.01); *C08F 2500/02* (2013.01); *G01N 2030/025* (2013.01); *Y02P 20/52* (2015.11)

(56) References Cited

U.S. PATENT DOCUMENTS

| | | | |
|---|---|---|---|
| 4,518,814 A * | 5/1985 | Knudsen | B01J 31/2226 |
| | | | 585/523 |
| 4,528,416 A | 7/1985 | Lutz | |
| 5,198,563 A | 3/1993 | Reagen et al. | |
| 5,376,612 A | 12/1994 | Reagen et al. | |
| 6,930,218 B2 | 8/2005 | Tembe et al. | |
| 7,964,763 B2 | 6/2011 | Dixon et al. | |
| 9,802,874 B2 | 10/2017 | Han et al. | |
| 2003/0130551 A1* | 7/2003 | Drochon | B01J 31/04 |
| | | | 585/520 |
| 2011/0086991 A1* | 4/2011 | Dixon | B01J 31/18 |
| | | | 526/139 |

FOREIGN PATENT DOCUMENTS

| | | |
|---|---|---|
| EP | 0444505 B1 | 5/1995 |
| EP | 0608447 B1 | 10/2001 |

* cited by examiner

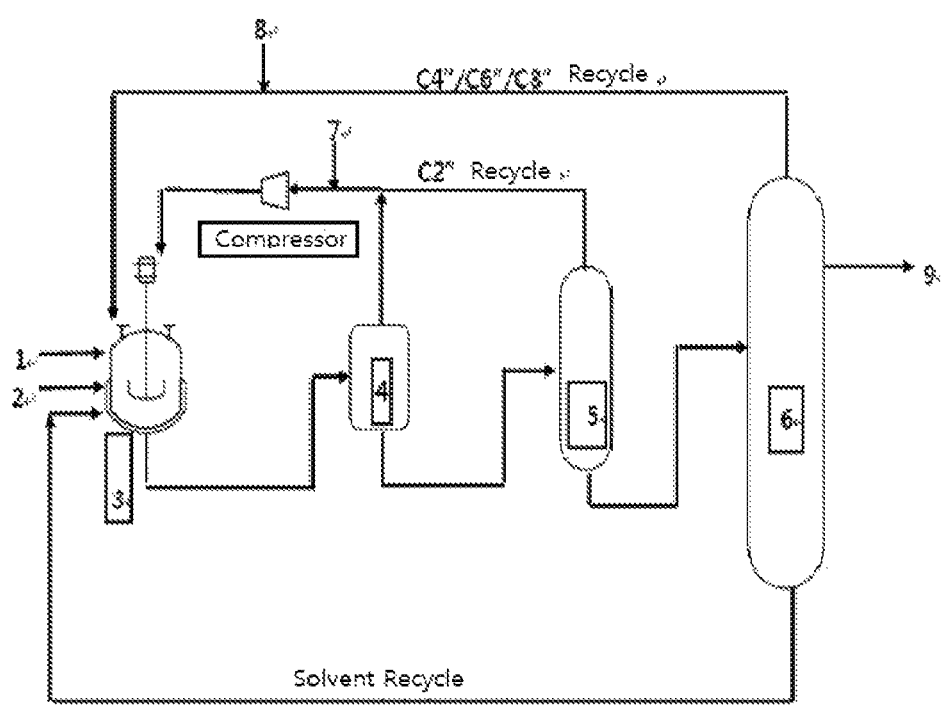

PROCESS FOR PRODUCING ETHYLENE OLIGOMERS

CROSS-REFERENCE TO RELATED APPLICATION

This application claims the benefit and priority of Korean Patent Application No. 10-2016-0171460 filed Dec. 15, 2016. The entire disclosure of the above application is incorporated herein by reference.

FIELD

The present disclosure relates to a process for producing ethylene oligomers which is a more efficient process for producing α-olefin including a double bond and having 10 to 12 carbon atoms via a new oligomerization method.

BACKGROUND

This section provides background information related to the present disclosure which is not necessarily prior art.

A conventional ethylene oligomerization technology is a catalyst technology for producing various α-olefins with Schulze-Flory or Poisson distribution and is also referred to as a full-range catalyst technology in the art. A catalyst technology for more selectively producing 1-butene, 1-hexene, or 1-octene is also referred to as an on-purpose technology. In recent years, a catalyst technology for more selectively producing 1-hexene or 1-octene has been greatly advanced.

The use of 1-butene, 1-hexene, or 1-octene has been greatly expanded to function as a co-monomer in production of linear low-density polyolefin. The use of the other various α-olefins having 10 or more carbon atoms is being expanded to serve as materials of detergent alcohols, lubricants for oil field, or wax, and the amount of the other α-olefins used is being greatly increased. The full-range catalyst technology has a long history, and a representative example thereof is a Ni-based catalyst being used in a SHOP processor developed by Shell. In this regard, EP0,177,999 and U.S. Pat. No. 3,676,523 illustrate a catalyst system from a diphenylphosphino acetic acid ligand and a Ni compound, and U.S. Pat. No. 4,528,416 illustrates a method of oligomerization of the catalyst in a mono-alcohol or diol solvent. Besides, DE1,443,927 and U.S. Pat. No. 3,906,053 illustrate a method of oligomerization of ethylene under a high ethylene pressure using a trialkyl aluminum catalyst. A method of oligomerization of ethylene with a catalyst system including zirconium alkoxide, alcohol, and an aluminum compound in the presence of solvents of toluene, cylcohexane, and normal-octane is illustrated in U.S. Pat. No. 6,930,218. However, the above-described catalysts have relatively low catalytic activity. EP0,444,505 discloses a processor for producing α-olefin using a Ziegler catalyst. The production of α-olefin is carried out efficiently but requires a relatively high ethylene pressure and a high temperature.

In recent years, the on-purpose catalyst technology of selectively trimerizing or tetramerizing ethylene into 1-hexene or 1-octene using various catalyst technologies has been greatly advanced, and most catalysts are based on chromium catalysts. As disclosed in U.S. Pat. Nos. 5,198,563, 5,376,612, and EP0,608,447, a high-activity and high-selectivity ethylene trimerization catalyst system commercialized by Phillips is based on a trivalent chromium compound, a pyrrole compound, and aluminum alkyl. In recent years, it has been disclosed that a chromium-based catalyst containing a chelate ligand including hetero atoms of phosphorous and nitrogen selectively trimerizes or tetramerizes ethylene into 1-hexene or 1-octene (U.S. Pat. No. 7,964,763), and examples of the catalyst include (phenyl)$_2$PN(isopropyl)P (phenyl)$_2$. The above-described prior art technologies are limited to the selective production of mainly 1-hexene or 1-octene α-olefin with a chromium catalyst containing a chelate ligand including hetero atoms and the chelate ligand is limited to a PNP backbone structure such as $(R_1)(R_2)P—N(R_5)—P(R_3)(R_4)$. Also, a high-selectivity tetramerization catalyst system is disclosed in KR1,074,202 and based on a catalyst system including a chromium compound, a di-phosphine ligand with a —P—C—C—P— backbone structure, and a co-catalyst compound.

As can be seen from the above description, the development of the full-range or on-purpose α-olefin production technology has been based on the advancement of various catalyst technologies, particularly a new ligand structure, and various requirements of α-olefins for development of various applications and uses need an improved catalyst and an improved process for producing ethylene oligomers.

SUMMARY

This section provides a general summary of the disclosure, and is not a comprehensive disclosure of its full scope or all of its features.

The present disclosure has been made in an effort to provide a process for producing ethylene oligomers which is a more efficient process for producing α-olefin including a double bond and having 10 to 12 carbon atoms via a new oligomerization method. More particularly, the present disclosure provides a process for producing α-olefin which has the selectivity of α-olefin having 10 to 12 carbon atoms and has an improved purity, as also described above in Background.

A catalyst used in the present disclosure includes a transition metal or transition metal precursor suitable for producing α-olefin, a ligand with a backbone structure expressed by the following Chemical Formula 1, and a co-catalyst.

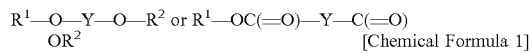
[Chemical Formula 1]

Herein, $R^1$, $R^2$ are each independently hydrocarbyl, substituted hydrocarbyl, heterohydrocarbyl, or substituted heterohydrocarbyl, and Y represents a group connecting O or C(=O)O and is hydrocarbyl, substituted hydrocarbyl, heterohydrocarbyl, or substituted heterohydrocarbyl.

Through an in-depth study, it was found that the present disclosure can be achieved best via a one-stage oligomerization reaction or a two-stage oligomerization reaction.

A more efficient process for producing ethylene oligomers that facilitates the production of α-olefin including a double bond and having 10 to 12 carbon atoms via a new oligomerization method according to the present disclosure and more particularly, a process for producing α-olefin which has the selectivity of α-olefin having 10 to 12 carbon atoms and has an improved purity will be described below.

A catalyst system for ethylene oligomerization according to the present disclosure includes a transition metal or transition metal precursor, a ligand with a backbone structure of $R^1$—O—Y—O—$R^2$ or $R^1$—OC(=O)—Y—C(=O) OR$^2$, and a co-catalyst, and the ligand with a backbone structure of $R^1$—O—Y—O—$R^2$ or $R^1$—OC(=O)—Y—C (=O)OR$^2$ is expressed by the following Chemical Formula 1.

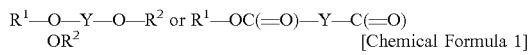

Herein, $R^1$, $R^2$ are each independently hydrocarbyl, substituted hydrocarbyl, heterohydrocarbyl, or substituted heterohydrocarbyl, and Y represents a group connecting O or C(=O)O and is hydrocarbyl, substituted hydrocarbyl, heterohydrocarbyl, or substituted heterohydrocarbyl.

Herein, $R^1$ and $R^2$ are each independently a hydrocarbyl group, a substituted hydrocarbyl group, or a substituted heterohydrocarbyl group adjacent to O or C(=O)O, and these arbitrary substituents may be non-electron donors. These substituents may be nonpolar groups.

Preferably, $R^1$ and $R^2$ may be substituted aromatic groups or substituted heteroaromatic groups which do not include non-electron donors on atoms adjacent to the atom bonded to an O atom or C(=O)O group.

Preferred examples of $R^1$ and $R^2$ may be each independently selected from the group consisting of phenyl, benzyl, naphthyl, anthracenyl, mesityl, methyl, ethyl, propyl, isopropyl, butyl, isobutyl, tertiary butyl, cyclohexyl, 4-methylcyclohexyl, 4-ethylcyclohexyl, 4-isopropylcyclohexyl, tolyl, xylyl, 4-methylphenyl, 4-ethylphenyl, 4-isopropylphenyl, 4-t-butylphenyl, 4-methoxyphenyl, 4-isopropoxyphenyl, cumyl, methoxy, ethoxy, phenoxy, tolyloxy, dimethylamino, thiomethyl, trimethylsilyl, and dimethylhydrazyl. Preferably, $R^1$ and $R^2$ may be each independently selected from the group consisting of methyl, ethyl, propyl, isopropyl, butyl, isobutyl, tertiary butyl phenyl, tolyl, biphenyl, naphthyl, cyclohexyl, 4-methylphenyl, 4-ethylphenyl, 4-isopropylphenyl, 4-t-butylphenyl, 4-methoxyphenyl, and 4-isopropoxyphenyl.

$R^1$ and $R^2$ may be each independently an aromatic group and a substituted aromatic group, and each of $R^1$ and $R^2$ may be substituted with a non-electron donor group on at least one atom thereof, which is not adjacent to the atom bonded to an O atom or C(=O)O group. Further, each of $R^1$ and $R^2$ may be substituted with a nonpolar group on at least one atom thereof, which is not adjacent to the atom bonded to $Z^1$, $Z^2$ atoms or groups.

Y may be a group connecting an O atom or C(=O)O group, and may be a hydrocarbyl group, a substituted hydrocarbyl group, or a substituted heterohydrocarbyl group. These substituents may be nonpolar groups. Examples of Y may include methylene, 1,2-ethane, 1,2-phenylene, 1,3-propane, 1,4-butane, 1,5-pentane, and the like.

Examples of the ligand with a backbone structure of $R^1$—O—Y—O—$R^2$ or $R^1$—OC(=O)—Y—C(=O)O$R^2$ according to the present disclosure may include the following structure. However, the following structure example is provided only for illustrating the present disclosure, but does not limit the protective scope of Chemical Formula 1 of the present disclosure.

Representative structure examples of Chemical Formula 1 may include diether and diester compounds. The diether compounds may include 1,3-diether-based compounds.

Herein, $R^1$ and $R^2$ are identical or different and represent C1-C18 alkyl groups, C3-C18 cycloalkyl groups, or C7-C18 aryl radical groups; and $R^3$ and $R^4$ are identical or different and represent C1-C4 alkyl radical groups or cyclic or polycyclic groups in which the carbon atom at position 2 contains 2 or 3 unsaturated bonds and which have 5, 6, or 7 carbon atoms.

Examples of the 1,3-diether-based compounds may include 2,2-diisobutyl-1,3-dimethoxypropane, 2-isopropyl-2-isobutyl-1,3-dimethoxypropane, 2-isopropyl-2-isopentyl-1,3-dimethoxypropane, 2,2-dicyclohexyl-1,3-dimethoxypropane, 9,9-bis(methoxymethyl)fluorene, and the like.

Further, the diether compounds may include cyclic polyene 1,3-diether. Examples of the cyclic polyene 1,3-diether may include 1,1-bis(methoxymethyl)-cyclopentadiene, 1,1-bis(methoxymethyl)-2,3,4,5-tetramethylcyclopentadiene, 1,1-bis(methoxymethyl)-2,3,4,5-tetraphenylcyclopentadiene, 1,1-bis(methoxymethyl)-2,3,4,5-tetrafluorocyclopentadiene, 1,1-bis(methoxymethyl)-3,4-dicyclopentylcyclopentadiene, 1,1-bis(methoxymethyl)indene, 1,1-bis(methoxymethyl)-2,3-dimethylindene, 1,1-bis(methoxymethyl)-4,5,6,7-tetrahydroindene, 1,1-bis(methoxymethyl)-2,3,6,7-tetrafluoroindene, 1,1-bis(methoxymethyl)-4,7-dimethylindene, 1,1-bis(methoxymethyl)-3,6-dimethylindene, 1,1-bis(methoxymethyl)-4-phenylindene, 1,1-bis(methoxymethyl)-4-phenyl-2-methylindene, 1,1-bis(methoxymethyl)-4-cyclohexylindene, 1,1-bis(methoxymethyl)-7-(3,3,3-trifluoropropyl)indene, 1,1-bis(methoxymethyl)-7-trimethylsilylindene, 1,1-bis(methoxymethyl)-7-trifluoromethylindene, 1,1-bis(methoxymethyl)-4,7-dimethyl-4,5,6,7-tetrahydroindene, 1,1-bis(methoxymethyl)-7-methylindene, 1,1-bis(methoxymethyl)-7-cyclopentylindene, 1,1-bis(methoxymethyl)-7-isopropylindene, 1,1-bis(methoxymethyl)-7-cyclohexylindene, 1,1-bis(methoxymethyl)-7-t-butylindene, 1,1-bis(methoxymethyl)-7-t-butyl-2-methylindene, 1,1-bis(methoxymethyl)-7-phenylindene, 1,1-bis(methoxymethyl)-2-phenylindene, 1,1-bis(methoxymethyl)-1H-benz[e]indene, 1,1-bis(methoxymethyl)-1H-2-methylbenz[e]indene, 9,9-bis(methoxymethyl)fluorene, 9,9-bis(methoxymethyl)-2,3,6,7-tetramethylfluorene, 9,9-bis(methoxymethyl)-2,3,4,5,6,7-hexafluorofluorene, 9,9-bis(methoxymethyl)-2,3-benzofluorene, 9,9-bis(methoxymethyl)-2,3,6,7-dibenzofluorene, 9,9-bis(methoxymethyl)-2,7-diisopropylfluorene, 9,9-bis(methoxymethyl)-1,8-dichlorofluorene, 9,9-bis(methoxymethyl)-2,7-dicyclopentylfluorene, 9,9-bis(methoxymethyl)-1,8-difluorofluorene, 9,9-bis(methoxymethyl)-1,2,3,4-tetrahydrofluorene, 9,9-bis(methoxymethyl)-1,2,3,4,5,6,7,8-octahydrofluorene, 9,9-bis(methoxymethyl)-4-t-butylfluorene, 1,1-bis(1'-butoxyethyl)-cyclopentadiene, 1,1-bis(1'-isopropoxy-n-propyl)cyclopentadiene, 1-methoxymethyl-1-(1'-methoxyethyl)-2,3,4,5-tetramethylcyclopentadiene, 1,1-bis(α-methoxybenzyl)indene, 1,1-bis(phenoxymethyl)indene, 1,1-bis(1'-methoxyethyl)-5,6-dichloroindene, 1,1-bis(phenoxymethyl)-3,6-dicyclohexylindene, 1-methoxymethyl-1-(1'-methoxyethyl)-7-t-butylindene, 1,1-bis[2-(2'-methoxypropyl)]-2-methylindene, 3,3-bis(methoxymethyl)-3H-2-methylbenz[e]indene, 9,9-bis(α-methoxybenzyl)fluorene, 9,9-bis(1'-isopropoxy-n-butyl)-4,5-diphenylfluorene, 9,9-bis(1'-methoxyethyl)fluorene, 9-(methoxymethyl)-9-(1'-methoxyethyl)-2,3,6,7-tetrafluorofluorene, 9-methoxymethyl-9-penthoxymethylfluorene; 9-methoxymethyl-9-ethoxymethylfluorene, 9-methoxymethyl-9-(1'-methoxyethyl)-fluorene, 9-methoxymethyl-9-[2-(2-methoxypropyl)]-fluorene, 1,1-bis(methoxymethyl)-2,5-cyclohexadiene, 1,1-bis(methoxymethyl)benzonaphthene, 7,7-bis(methoxymethyl)-2,5-norbornanediene, 9,9-bis(methoxymethyl)-1,4-methane dihydronaphthalene, 4,4-bis(methoxymethyl)-4H-cyclopenta[d, e, f]phenanthrene, 9,9-bis(methoxymethyl)-9,10-dihydroanthracene, 7,7-bis(methoxymethyl)-7H-benz[d,e]anthracene, 1,1-bis(methoxymethyl)-1,2-dihydronaphthalene, 4,4-bis (methoxymethyl)-1-phenyl-3,4-dihydronaphthalene, 4,4-bis(methoxymethyl)-1-phenyl-1,4-dihydronaphthalene, 5,5-bis(methoxymethyl)-1,3,6-cycloheptatriene, 5,5-bis(methoxymethyl)-10,11-dihydro-5H-dibenzo[a,d]cycloheptene, 5,5-bis(methoxymethyl)-5H-dibenzo[a,d]cycloheptene, 9,9-bis(methoxymethyl)xanthene, 9,9-bis(methoxymethyl)-2,3,6,7-tetramethylxanthene, 9,9-bis(1'-methoxyisobutyl)thioxanthene, 4,4-bis(methoxymethyl)-1,4-pyrane, 9,9-bis(methoxymethyl)-N-t-butyl-9,10-dihydroacrydine, 4,4-bis(methoxymethyl)-1,4-chromene, 4,4-bis(methoxymethyl)-1,2,4-oxazine, 1,1-bis(methoxymethyl)benzo-2,3,1-oxazine, 5,5-bis(methoxymethyl)-1,5-pyridine, 5,5-bis(methoxymethyl)-6,7-dimethyl-1,5-pyridine, 2,2-bis(methoxymethyl)-3,4,5-trifluoroisopyrrole, 4,4-bis(1'-methoxyethyl)benzo-N-phenyl-1,4-dihydropyridine, and the like.

The dicarboxylic acid ester compounds may have various structures. One example is a benzene-1,2-dicarboxylic acid ester compound.

Specific examples of the benzene-1,2-dicarboxylic acid ester compound may include dimethylphthalate, diethylphthalate, dinormalpropylphthalate, diisopropylphthalate, dinormalbutylphthalate, diisobutylphthalate, dinormalpentylphthalate, di(2-methylbutyl)phthalate, di(3-methylbutyl)phthalate, dineopentylphthalate, dinormalhexylphthalate, di(2-methylpentyl)phthalate, di(3-methylpentyl)phthalate, diisohexylphthalate, dineohexylphthalate, di(2,3-dimethylbutyl)phthalate, dinormalheptylphthalate, di(2-methylhexyl)phthalate, di(2-ethylpentyl)phthalate, diisoheptylphthalate, dineoheptylphthalate, dinormaloctylphthalate, di(2-methylheptyl)phthalate, diisooctylphthalate, di(3-ethylhexyl)phthalate, dineooctylphthalate, dinormalnonylphthalate, diisononylphthalate, dinormaldecylphthalate, and diisodecylphthalate.

Further, the dicarboxylic acid ester may include malonate, succinate, glutarate, pivalate, adipate, sebacate, malate, naphthalene dicarboxylate, trimellitate, benzene-1,2,3-tricarboxylate, pyromellitate, and carbonate. Examples thereof may include diethyl malonate, dibutyl malonate, dimethylsuccinate, diethylsuccinate, dinormalpropyl succinate, diisopropylsuccinate, 1,1-dimethyl-dimethylsuccinate, 1,1-dimethyl-diethylsuccinate, 1,1-dimethyl-dinormalpropylsuccinate, 1,1-dimethyl-diisopropylsuccinate, 1,2-dimethyl-dimethylsuccinate, 1,2-dimethyl-diethylsuccinate, ethyl-dimethylsuccinate, ethyl-diethylsuccinate, ethyl-dinormalpropylsuccinate, ethyl-diisopropylsuccinate, 1,1-diethyl-dimethylsuccinate, 1,1-diethyl-diethylsuccinate, 1,1-diethyl-dimethylsuccinate, 1,2-diethyl-dimethylsuccinate, 1,2-diethyl-diethylsuccinate, 1,2-diethyl-dinormalpropylsuccinate, 1,2-diethyl-diisopropylsuccinate, normalpropyl-dimethylsuccinate, normalpropyl-diethylsuccinate, normalpropyl-dinormalpropylsuccinate, normalpropyl-diisopropylsuccinate, isopropyl-dimethylsuccinate, isopropyl-diethylsuccinate, isopropyl-dinormalpropylsuccinate, isopropyl-diisopropylsuccinate, 1,2-diisopropyl-dimethylsuccinate, 1,2-diisopropyl-diethylsuccinate, 1,2-diisopropyl-dinormalpropylsuccinate, 1,2-diisopropyl-diisopropylsuccinate, normalbutyl-dimethylsuccinate, normalbutyl-diethylsuccinate, normalbutyl-dinormalpropylsuccinate, normalbutyl-diisopropylsuccinate, isobutyl-dimethyl succinate, isobutyl-diethylsuccinate, isobutyl-dinormalpropylsuccinate, isobutyl-diisopropylsuccinate, 1,2-dinormalbutyl-dimethylsuccinate, 1,2-dinormalbutyl-diethylsuccinate, 1,2-dinormalbutyl-dinormalpropylsuccinate, 1,2-dinormalbutyl-diisopropylsuccinate, 1,2-dinormalbutyl-dimethylsuccinate, 1,2-diisobutyl-dimethylsuccinate, 1,2-diisobutyl-diethylsuccinate, 1,2-diisobutyl-dinormalpropylsuccinate, 1,2-diisobutyl-diisopropylsuccinate, diethyl adipate, dibutyl adipate, diethyl sebacate, dibutyl sebacate, diethyl malate, di-n-butyl malate, diethyl naphthalene dicarboxylate, dibutyl naphthalene dicarboxylate, triethyl trimellitate, tributyl trimellitate, triethyl benzene-1,2,3-tricarboxylate, tributyl benzene-1,2,3-tricarboxylate, tetraethyl pyromellitate, tetrabutyl pyromellitate, and the like.

The dicarboxylic acid ester compound may also include an example having the following structure.

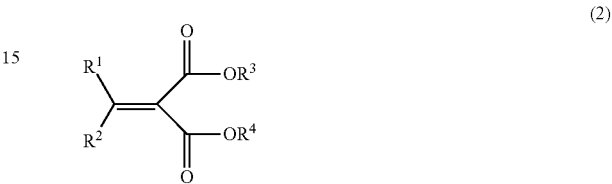

(2)

Herein, $R^1$ and $R^2$ are each independently hydrogen or a linear or branched alkyl group having 1 to 20 carbon atoms, a cyclic alkyl group or alkenyl group having 3 to 20 carbon atoms, an aryl group having 6 to 20 carbon atoms, or an arylalkyl group or alkylaryl group having 7 to 20 carbon atoms and are combined to form a cycle, and $R^3$ and $R^4$ are each independently a linear or branched alkyl group having 1 to 20 carbon atoms. Examples thereof may include diethyl 2-(1H-indene-2(3H)-ylidene)malonate, diethyl 2-(9H-fluorene-9-ylidene)malonate, diethyl 2-cyclobutylidene malonate, diethyl 2-cyclopentylidene malonate, diethyl 2-cyclohexylidene malonate, diethyl 2-methylene malonate, diethyl 2-ethylidene malonate, diethyl 2-propylidene malonate, diethyl 2-(2-methylpropylidene)malonate, diethyl 2-(2,2-dimethylpropylidene)malonate, diethyl 2-(cyclobutylmethylene)malonate, diethyl 2-(cyclopentylmethylene) malonate, diethyl 2-(cyclohexylmethylene)malonate, diethyl 2-(butane-2-ylidene)malonate, diethyl 2-(3-methylbutane-2-ylidene)malonate, diethyl 2-(3,3-dimethylbutane-2-ylidene)malonate, diethyl 2-(1-cyclobutylethylidene)malonate, diethyl 2-(1-cyclopentylethylidene)malonate, diethyl 2-(1-cyclohexylethylidene)malonate, diethyl 2-(2,4-dimethylpentane-3-ylidene)malonate, diethyl 2-(2,2,4,4,-tetramethylpentane-3-ylidene)malonate, diethyl 2-(dicyclobutylmethylene)malonate, diethyl 2-(dicyclopentylmethylene) malonate, diethyl 2-(dicyclohexylmethylene)malonate, dipropyl 2-(1H-indene-2(3H)-ylidene)malonate, dipropyl 2-(9H-fluorene-9-ylidene)malonate, dipropyl 2-cyclobutylidene malonate, dipropyl 2-cyclopentylidene malonate, dipropyl 2-cyclohexylidene malonate, dipropyl 2-methylene malonate, dipropyl 2-ethylidene malonate, dipropyl 2-propylidene malonate, dipropyl 2-(2-methylpropylidene)malonate, dipropyl 2-(2,2-dimethylpropylidene)malonate, dipropyl 2-(cyclobutylmethylene)malonate, dipropyl 2-(cyclopentylmethylene)malonate, dipropyl 2-(cyclohexylmethylene) malonate, dipropyl 2-(butane-2-ylidene) malonate, dipropyl 2-(3-methylbutane-2-ylidene)malonate, dipropyl 2-(3,3-dimethylbutane-2-ylidene)malonate, dipropyl 2-(1-cyclobutylethylidene)malonate, dipropyl 2-(1-cyclopentylethylidene)malonate, dipropyl 2-(1-cyclohexylethylidene) malonate, dipropyl 2-(2,4-dimethylpentane-3-ylidene) malonate, dipropyl 2-(2,2,4,4,-tetramethylpentane-3-ylidene)malonate, dipropyl 2-(dicyclobutylmethylene) malonate, dipropyl 2-(dicyclopentylmethylene)malonate, dipropyl 2-(dicyclohexylmethylene)malonate, diisopropyl 2-(1H-indene-2(3H)-ylidene)malonate, diisopropyl 2-(9H-fluorene-9-ylidene)malonate, diisopropyl 2-cyclobutylidene malonate, diisopropyl 2-cyclopentylidene malonate, diisopropyl 2-cyclohexylidene malonate, diisopropyl 2-methylene malonate, diisopropyl 2-ethylidene malonate, diisopropyl 2-propylidene malonate, diisopropyl 2-(2-methylpropylidene)malonate, diisopropyl 2-(2,2-dimethylpropylidene)malonate, diisopropyl 2-(cyclobutylmethylene)malonate, diisopropyl 2-(cyclopentylmethylene)malonate, diisopropyl 2-(cyclohexylmethylene)malonate, diisopropyl 2-(butane-2-ylidene)malonate, diisopropyl2-(3-methylbutane-2-ylidene)malonate, diisopropyl 2-(3,3-dimethylbutane-2-ylidene)malonate, diisopropyl 2-(1-cyclobutylethylidene)malonate, diisopropyl 2-(1-cyclopentylethylidene)malonate, diisopropyl 2-(1-cyclohexylethylidene)malonate, diisopropyl 2-(2,4-dimethylpentane-3-ylidene)malonate, diisopropyl 2-(2,2,4,4,-tetramethylpentane-3-ylidene)malonate, diisopropyl 2-(dicyclobutylmethylene)malonate, diisopropyl 2-(dicyclopentylmethylene)malonate, diisopropyl 2-(dicyclohexylmethylene)malonate, dibutyl 2-(1H-indene-2(3H)-ylidene) malonate, dibutyl 2-(9H-fluorene-9-ylidene)malonate dibutyl 2-cyclobutylidene malonate, dibutyl 2-cyclopentylidene malonate, dibutyl 2-cyclohexylidene malonate, dibutyl 2-methylene malonate, dibutyl 2-ethylidene malonate, dibutyl 2-propylidene malonate, dibutyl 2-(2-methylpropylidene)malonate, dibutyl 2-(2,2-dimethylpropylidene)malonate, dibutyl 2-(cyclobutylmethylene)malonate, dibutyl 2-(cyclopentylmethylene)malonate, dibutyl 2-(cyclohexylmethylene)malonate, dibutyl 2-(butane-2-ylidene)malonate, dibutyl 2-(3-methylbutane-2-ylidene)malonate, dibutyl 2-(3,3-dimethylbutane-2-ylidene)malonate, dibutyl 2-(1-cyclobutylethylidene)malonate, dibutyl 2-(1-cyclopentylethylidene)malonate, dibutyl 2-(1-cyclohexylethylidene) malonate, dibutyl 2-(2,4-dimethylpentane-3-ylidene) malonate, dibutyl 2-(2,2,4,4,-tetramethylpentane-3-ylidene) malonate, dibutyl 2-(dicyclobutylmethylene)malonate, dibutyl 2-(dicyclopentylmethylene)malonate, dibutyl 2-(dicyclohexylmethylene)malonate, diisobutyl 2-(1H-indene-2 (3H)-ylidene)malonate, diisobutyl 2-(9H-fluorene-9-ylidene)malonate, diisobutyl 2-cyclobutylidene malonate, diisobutyl 2-cyclopentylidene malonate, diisobutyl 2-cyclohexylidene malonate, diisobutyl 2-methylene malonate, diisobutyl 2-ethylidene malonate, diisobutyl 2-propylidene malonate, diisobutyl 2-(2-methylpropylidene)malonate, diisobutyl 2-(2,2-dimethylpropylidene)malonate, diisobutyl 2-(cyclobutylmethylene)malonate, diisobutyl 2-(cyclopentylmethylene)malonate, diisobutyl 2-(cyclohexylmethylene) malonate, diisobutyl 2-(butane-2-ylidene)malonate, diisobutyl 2-(3-methylbutane-2-ylidene)malonate, diisobutyl 2-(3,3-dimethylbutane-2-ylidene)malonate, diisobutyl 2-(1-cyclobutylethylidene)malonate, diisobutyl 2-(1-cyclopentylethylidene)malonate, diisobutyl 2-(1-cyclohexylethylidene)malonate, diisobutyl 2-(2,4-dimethylpentane-3-ylidene)malonate, diisobutyl 2-(2,2,4,4,-tetramethylpentane-3-ylidene)malonate, diisobutyl 2-(dicyclobutylmethylene)malonate, diisobutyl 2-(dicyclopentylmethylene)malonate, diisobutyl 2-(dicyclohexylmethylene)malonate, and the like.

The dicarboxylic acid ester compound may include a bicycloalkanedicarboxylate-based or bicycloalkenedicarboxylate-based compound represented by General Formula 3, General Formula 4, General Formula 5, or General Formula 6 having the following structure.

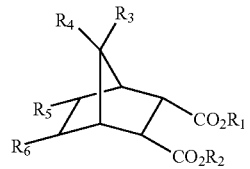
-(3)

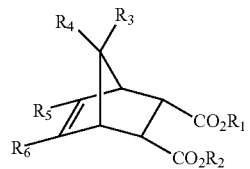
-(4)

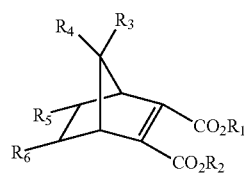
-(5)

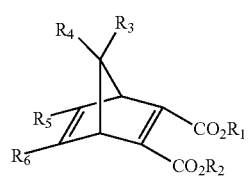
-(6)

Herein, $R_1$ and $R_2$ are identical to or different from each other and represent linear, branched, or cyclic alkyl groups or alkenyl groups having 1 to 20 carbon atoms, aryl groups having 6 to 20 carbon atoms, or arylalkyl groups or alkylaryl groups having 7 to 20 carbon atoms; and $R_3$, $R_4$, $R_5$ and $R_6$ are identical to or different from each other and represent hydrogen, linear, branched, or cyclic alkyl groups or alkenyl groups having 1 to 20 carbon atoms, aryl groups having 6 to 20 carbon atoms, or arylalkyl groups or alkylaryl groups having 7 to 20 carbon atoms.

Examples of the bicycloalkanedicarboxylate-based or bicycloalkenedicarboxylate-based compound represented by General Formula 3, General Formula 4, General Formula 5, or General Formula 6 may include bicyclo[2.2.1]heptane-2,3-dicarboxylic acid ethylhexylester, bicyclo[2.2.1]heptane-2,3-dicarboxylic acid dioctylester, bicyclo[2.2.1]heptane-2,3-dicarboxylic acid diisobutylester, bicyclo[2.2.1]heptane-2,3-dicarboxylic acid dibutylester, bicyclo[2.2.1]heptane-2,3-dicarboxylic acid diisopropylester, bicyclo[2.2.1]heptane-2,3-dicarboxylic acid dipropylester, bicyclo[2.2.1]heptane-2,3-dicarboxylic acid diethylester, bicyclo[2.2.1]heptane-2,3-dicarboxylic acid dimethylester, 7,7-dimethylbicyclo[2.2.1]heptane-2,3-dicarboxylic acid ethylhexylester, 7,7-dimethylbicyclo[2.2.1]heptane-2,3-dicarboxylic acid dioctylester, 7,7-dimethylbicyclo[2.2.1]heptane-2,3-dicarboxylic acid diisobutylester, 7,7-dimethylbicyclo[2.2.1]heptane-2,3-dicarboxylic acid dibutylester, 7,7-dimethylbicyclo[2.2.1]heptane-2,3-dicarboxylic acid diisopropylester, 7,7-dimethylbicyclo[2.2.1]heptane-2,3-dicarboxylic acid dipropylester, 7,7-dimethylbicyclo[2.2.1]heptane-2,3-dicarboxylic acid diethylester, 7,7-dimethylbicyclo[2.2.1]heptane-2,3-dicarboxylic acid dimethylester, 5-methylbicyclo[2.2.1]heptane-2,3-dicarboxylic acid ethylhexylester, 5-methylbicyclo[2.2.1]heptane-2,3-dicarboxylic acid dioctylester, 5-methylbicyclo[2.2.1]heptane-2,3-dicarboxylic acid diisobutylester, 5-methylbicyclo[2.2.1]heptane-2,3-dicarboxylic acid dibutylester, 5-methylbicyclo[2.2.1]heptane-2,3-dicarboxylic acid diisopropylester, 5-methylbicyclo[2.2.1]heptane-2,3-dicarboxylic acid dipropylester, 5-methylbicyclo[2.2.1]heptane-2,3-dicarboxylic acid diethylester, 5-methylbicyclo[2.2.1]heptane-2,3-dicarboxylic acid dimethylester, 6-methylbicyclo[2.2.1]heptane-2,3-dicarboxylic acid ethylhexylester, 6-methylbicyclo[2.2.1]heptane-2,3-dicarboxylic acid dioctylester, 6-methylbicyclo[2.2.1]heptane-2,3-dicarboxylic acid diisobutylester, 6-methylbicyclo[2.2.1]heptane-2,3-dicarboxylic acid dibutylester, 6-methylbicyclo[2.2.1]heptane-2,3-dicarboxylic acid diisopropylester, 6-methylbicyclo[2.2.1]heptane-2,3-dicarboxylic acid dipropylester, 6-methylbicyclo[2.2.1]heptane-2,3-dicarboxylic acid diethylester, 6-methylbicyclo[2.2.1]heptane-2,3-dicarboxylic acid dimethylester, 5,6-dimethylbicyclo[2.2.1]heptane-2,3-dicarboxylic acid ethylhexylester, 5,6-dimethylbicyclo[2.2.1]heptane-2,3-dicarboxylic acid dioctylester, 5,6-dimethylbicyclo[2.2.1]heptane-2,3-dicarboxylic acid diisobutylester, 5,6-dimethylbicyclo[2.2.1]heptane-2,3-dicarboxylic acid dibutylester, 5,6-dimethylbicyclo[2.2.1]heptane-2,3-dicarboxylic acid diisopropylester, 5,6-dimethylbicyclo[2.2.1]heptane-2,3-dicarboxylic acid dipropylester, 5,6-dimethylbicyclo[2.2.1]heptane-2,3-dicarboxylic acid diethylester, 5,6-dimethylbicyclo[2.2.1]heptane-2,3-dicarboxylic acid dimethylester, bicyclo[2.2.1]hept-5-ene-2,3-dicarboxylic acid ethylhexylester, bicyclo[2.2.1]hept-5-ene-2,3-dicarboxylic acid dioctylester, bicyclo[2.2.1]hept-5-ene-2,3-dicarboxylic acid diisobutylester, bicyclo[2.2.1]hept-5-ene-2,3-dicarboxylic acid dibutylester, bicyclo[2.2.1]hept-5-ene-2,3-dicarboxylic acid diisopropylester, bicyclo[2.2.1]hept-5-ene-2,3-dicarboxylic acid dipropylester, bicyclo[2.2.1]hept-5-ene-2,3-dicarboxylic acid diethylester, bicyclo[2.2.1]hept-5-ene-2,3-dicarboxylic acid dimethylester, 7,7-dimethylbicyclo[2.2.1]hept-5-ene-2,3-dicarboxylic acid ethylhexylester, 7,7-dimethylbicyclo[2.2.1]hept-5-ene-2,3-dicarboxylic acid dioctylester, 7,7-dimethylbicyclo[2.2.1]hept-5-ene-2,3-dicarboxylic acid diisobutylester, 7,7-dimethylbicyclo[2.2.1]hept-5-ene-2,3-dicarboxylic acid dibutylester, 7,7-dimethylbicyclo[2.2.1]hept-5-ene-2,3-dicarboxylic acid diisopropylester, 7,7-dimethylbicyclo[2.2.1]hept-5-ene-2,3-dicarboxylic acid dipropylester, 7,7-dimethylbicyclo[2.2.1]hept-5-ene-2,3-dicarboxylic acid diethylester, 7,7-dimethylbicyclo[2.2.1]hept-5-ene-2,3-dicarboxylic acid dimethylester, 5-methylbicyclo[2.2.1]hept-5-ene-2,3-dicarboxylic acid ethylhexylester, 5-methylbicyclo[2.2.1]hept-5-ene-2,3-dicarboxylic acid dioctylester, 5-methylbicyclo[2.2.1]hept-5-ene-2,3-dicarboxylic acid diisobutylester, 5-methylbicyclo[2.2.1]hept-5-ene-2,3-dicarboxylic acid dibutylester, 5-methylbicyclo[2.2.1]hept-5-ene-2,3-dicarboxylic acid diisopropylester, 5-methylbicyclo[2.2.1]hept-5-ene-2,3-dicarboxylic acid dipropylester, 5-methylbicyclo[2.2.1]hept-5-ene-2,3-dicarboxylic acid diethylester, 5-methylbicyclo[2.2.1]hept-5-ene-2,3-dicarboxylic acid dimethylester, 6-methylbicyclo[2.2.1]hept-5-ene-2,3-dicarboxylic acid ethylhexylester, 6-methylbicyclo[2.2.1]hept-5-ene-2,3-dicarboxylic acid dioctylester, 6-methylbicyclo[2.2.1]hept-5-ene-2,3-dicarboxylic acid diisobutylester, 6-methylbicyclo[2.2.1]hept-5-ene-2,3-dicarboxylic acid dibutylester, 6-methylbicyclo[2.2.1]hept-5-ene-2,3-dicarboxylic acid diisopropylester, 6-methylbicyclo[2.2.1]hept-5-ene-2,3-dicarboxylic acid dipropylester, 6-methylbicyclo[2.2.1]hept-5-ene-2,3-dicarboxylic acid diethylester, 6-methylbicyclo[2.2.1]hept-5-ene-2,3-dicarboxylic acid dimethylester, 5,6-dimethylbicyclo[2.2.1]hept-5-ene-2,3-dicarboxylic acid ethylhexylester, 5,6-dimethylbicyclo[2.2.1]hept-5-ene-2,3-dicarboxylic acid dioctylester, 5,6-dimethylbicyclo[2.2.1]hept-5-ene-2,3-dicarboxylic acid diisobutylester, 5,6-dimethylbicyclo[2.2.1]hept-5-ene-2,3-dicarboxylic acid dibutylester, 5,6-dimethylbicyclo[2.2.1]hept-5-ene-2,3-dicarboxylic acid diisopropylester, 5,6-dimethylbicyclo[2.2.1]hept-5-ene-2,3-dicarboxylic acid dipropylester, 5,6-dimethylbicyclo[2.2.1]hept-5-ene-2,3-dicarboxylic acid diethylester, 5,6-dimethylbicyclo[2.2.1]hept-5-ene-2,3-dicarboxylic acid dimethylester, bicyclo[2.2.1]hept-2-ene-2,3-dicarboxylic acid ethylhexylester, bicyclo[2.2.1]hept-2-ene-2,3-dicarboxylic acid dioctylester, bicyclo[2.2.1]hept-2-ene-2,3-dicarboxylic acid diisobutylester, bicyclo[2.2.1]hept-2-ene-2,3-dicarboxylic acid dibutylester, bicyclo[2.2.1]hept-2-ene-2,3-dicarboxylic acid diisopropylester, bicyclo[2.2.1]hept-2-ene-2,3-dicarboxylic acid dipropylester, bicyclo[2.2.1]hept-2-ene-2,3-dicarboxylic acid diethylester, bicyclo[2.2.1]hept-2-ene-2,3-dicarboxylic acid dimethylester, 7,7-dimethylbicyclo[2.2.1]hept-2-ene-2,3-dicarboxylic acid ethylhexylester, 7,7-dimethylbicyclo[2.2.1]hept-2-ene-2,3-dicarboxylic acid dioctylester, 7,7-dimethylbicyclo[2.2.1]hept-2-ene-2,3-dicarboxylic acid diisobutylester, 7,7-dimethylbicyclo[2.2.1]hept-2-ene-2,3-dicarboxylic acid dibutylester, 7,7-dimethylbicyclo[2.2.1]hept-2-ene-2,3-dicarboxylic acid diisopropylester, 7,7-dimethylbicyclo[2.2.1]hept-2-ene-2,3-dicarboxylic acid dipropylester, 7,7-dimethylbicyclo[2.2.1]hept-2-ene-2,3-dicarboxylic acid diethylester, 7,7-dimethylbicyclo[2.2.1]hept-2-ene-2,3-dicarboxylic acid dimethylester, 5-methylbicyclo[2.2.1]hept-2-ene-2,3-dicarboxylic acid ethylhexylester, 5-methylbicyclo[2.2.1]hept-2-ene-2,3-dicarboxylic acid dioctylester, 5-methylbicyclo[2.2.1]hept-2-ene-2,3-dicarboxylic acid diisobutylester, 5-methylbicyclo[2.2.1]hept-2-ene-2,3-dicarboxylic acid dibutylester, 5-methylbicyclo[2.2.1]hept-2-ene-2,3-dicarboxylic acid diisopropylester, 5-methylbicyclo[2.2.1]hept-2-ene-2,3-dicarboxylic acid dipropylester, 5-methylbicyclo[2.2.1]hept-2-ene-2,3-dicarboxylic acid diethylester, 5-methylbicyclo[2.2.1]hept-2-ene-2,3-dicarboxylic acid dimethylester, 6-methylbicyclo[2.2.1]hept-2-ene-2,3-dicarboxylic acid ethylhexylester, 6-methylbicyclo[2.2.1]hept-2-ene-2,3-dicarboxylic acid dioctylester, 6-methylbicyclo[2.2.1]hept-2-ene-2,3-dicarboxylic acid diisobutylester, 6-methylbicyclo[2.2.1]hept-2-ene-2,3-dicarboxylic acid dibutylester, 6-methylbicyclo[2.2.1]hept-2-ene-2,3-dicarboxylic acid diisopropylester, 6-methylbicyclo[2.2.1]hept-2-ene-2,3-dicarboxylic acid dipropylester, 6-methylbicyclo[2.2.1]hept-2-ene-2,3-dicarboxylic acid diethylester, 6-methylbicyclo[2.2.1]hept-2-ene-2,3-dicarboxylic acid dimethylester, 5,6-dimethylbicyclo[2.2.1]hept-2-ene-2,3-dicarboxylic acid ethylhexylester, 5,6-dimethylbicyclo[2.2.1]hept-2-ene-2,3-dicarboxylic acid dioctylester, 5,6-dimethylbicyclo[2.2.1]hept-2-ene-2,3-dicarboxylic acid diisobutylester, 5,6-dimethylbicyclo[2.2.1]hept-2-ene-2,3-dicarboxylic acid dibutylester, 5,6-dimethylbicyclo[2.2.1]hept-2-ene-2,3-dicarboxylic acid diisopropylester, 5,6-dimethylbicyclo[2.2.1]hept-2-ene-2,3-dicarboxylic acid dipropylester, 5,6-dimethylbicyclo[2.2.1]hept-2-ene-2,3-dicarboxylic acid diethylester, 5,6-dimethylbicyclo[2.2.1]hept-2-ene-2,3-dicarboxylic acid dimethylester, bicyclo[2.2.1]hept-2,5-dien-2,3-dicarboxylic acid ethylhexylester, bicyclo[2.2.1]hept-2,5-dien-2,3-dicarboxylic acid dioctylester, bicyclo[2.2.1]hept-2,5-dien-2,3-dicarboxylic acid diisobutylester, bicyclo[2.2.1]hept-2,5-dien-2,3-dicarboxylic acid dibutylester, bicyclo[2.2.1]hept-2,5-dien-2,3-dicarboxylic acid diisopropylester, bicyclo[2.2.1]hept-2,5-dien-2,3-dicarboxylic acid dipropylester, bicyclo[2.2.1]hept-2,5-dien-2,3-dicarboxylic acid diethylester, bicyclo[2.2.1]hept-2,5-dien-2,3-dicarboxylic acid dimethylester, 7,7- dimethylbicyclo[2.2.1]hept-2,5-dien-2,3-dicarboxylic acid ethylhexylester, 7,7-dimethylbicyclo[2.2.1]hept-2,5-dien-2,3-dicarboxylic acid dioctylester, 7,7-dimethylbicyclo[2.2.1]hept-2,5-dien-2,3-dicarboxylic acid diisobutylester, 7,7-dimethylbicyclo[2.2.1]hept-2,5-dien-2,3-dicarboxylic acid dibutylester, 7,7-dimethylbicyclo[2.2.1]hept-2,5-dien-2,3-dicarboxylic acid diisopropylester, 7,7-dimethylbicyclo[2.2.1]hept-2,5-dien-2,3-dicarboxylic acid dipropylester, 7,7-dimethylbicyclo[2.2.1]hept-2,5-dien-2,3-dicarboxylic acid diethylester, 7,7-dimethylbicyclo[2.2.1]hept-2,5-dien-2,3-dicarboxylic acid dimethylester, 5-methylbicyclo[2.2.1]hept-2,5-dien-2,3-dicarboxylic acid ethylhexylester, 5-methylbicyclo[2.2.1]hept-2,5-dien-2,3-dicarboxylic acid dioctylester, 5-methylbicyclo[2.2.1]hept-2,5-dien-2,3-dicarboxylic acid diisobutylester, 5-methylbicyclo[2.2.1]hept-2,5-dien-2,3-dicarboxylic acid dibutylester, 5-methylbicyclo[2.2.1]hept-2,5-dien-2,3-dicarboxylic acid diisopropylester, 5-methylbicyclo[2.2.1]hept-2,5-dien-2,3-dicarboxylic acid dipropylester, 5-methylbicyclo[2.2.1]hept-2,5-dien-2,3-dicarboxylic acid diethylester, 5-methylbicyclo[2.2.1]hept-2,5-dien-2,3-dicarboxylic acid dimethylester, 6-methylbicyclo[2.2.1]hept-2,5-dien-2,3-dicarboxylic acid ethylhexylester, 6-methylbicyclo[2.2.1]hept-2,5-dien-2,3-dicarboxylic acid dioctylester, 6-methylbicyclo[2.2.1]hept-2,5-dien-2,3-dicarboxylic acid diisobutylester, 6-methylbicyclo[2.2.1]hept-2,5-dien-2,3-dicarboxylic acid dibutylester, 6-methylbicyclo[2.2.1]hept-2,5-dien-2,3-dicarboxylic acid diisopropylester, 6-methylbicyclo[2.2.1]hept-2,5-dien-2,3-dicarboxylic acid dipropylester, 6-methylbicyclo[2.2.1]hept-2,5-dien-2,3-dicarboxylic acid diethylester, 6-methylbicyclo[2.2.1]hept-2,5-dien-2,3-dicarboxylic acid dimethylester, 5,6-dimethylbicyclo[2.2.1]hept-2,5-dien-2,3-dicarboxylic acid ethylhexylester, 5,6-dimethyl bicyclo[2.2.1]hept-2,5-dien-2,3-dicarboxylic acid dioctylester, 5,6-dimethylbicyclo[2.2.1]hept-2,5-dien-2,3-dicarboxylic acid diisobutylester, 5,6-dimethylbicyclo[2.2.1]hept-2,5-dien-2,3-dicarboxylic acid dibutylester, 5,6-dimethylbicyclo[2.2.1]hept-2,5-dien-2,3-dicarboxylic acid diisopropylester, 5,6-dimethylbicyclo[2.2.1]hept-2,5-dien-2,3-dicarboxylic acid dipropylester, 5,6-dimethylbicyclo[2.2.1]hept-2,5-dien-2,3-dicarboxylic acid diethylester, 5,6-dimethylbicyclo[2.2.1]hept-2,5-dien-2,3-dicarboxylic acid dimethylester, and the like.

The transition metal or transition metal precursor according to the present disclosure may be selected from the group consisting of Group 3 to Group 10 in the periodic table, and may preferably be chromium. In the catalyst for ethylene oligomerization according to the present disclosure, the transition metal compound may be a simple inorganic or organic salt, a metal-coordinated complex, or a metallo-organic complex, and may preferably be chromium or a chromium precursor. Preferably, the chromium or chromium precursor may be selected from the group consisting of chromium(III)acetylacetonate, chromium trichloride tristetrahydrofuran, and chromium(III)2-ethylhexanoate.

The catalyst system according to the present disclosure may be produced through a process of producing a ligand coordination complex (catalyst precursor) from the transition metal compound and the $R^1$—O—Y—O—$R^2$ or $R^1$—OC(=O)—Y—C(=O)O$R^2$ backbone structure ligand. A coordination complex produced using the $R^1$—O—Y—O—$R^2$ or $R^1$—OC(=O)—Y—C(=O)O$R^2$ backbone structure ligand and the transition metal compound may be added to a reaction mixture, or the $R^1$—O—Y—O—$R^2$ or $R^1$—OC(=O)—Y—C(=O)O$R^2$ backbone structure ligand and the transition metal compound may be separately added into a reactor, and, thus, a ligand coordination complex with a backbone structure of $R^1$—O—Y—O—$R^2$ or $R^1$—OC(=O)—Y—C(=O)O$R^2$ can be produced. The fact that the in-situ ligand coordination complex with a backbone structure of $R^1$—O—Y—O—$R^2$ or $R^1$—OC(=O)—Y—C(=O)O$R^2$ is produced means that the complex is produced in a medium in which a catalytic reaction is conducted. In order to produce the ligand coordination complex, the transition metal compound and the $R^1$—O—Y—O—$R^2$ or $R^1$—OC(=O)—Y—C(=O)O$R^2$ backbone structure ligand are mixed such that a combination ratio of the metal to the ligand is typically about 0.01:1 to 100:1, preferably about 0.1:1 to 10:1, and more preferably 0.5:1 to 2:1.

The co-catalyst according to the present disclosure may be an arbitrary compound used to produce an active catalyst when it is mixed with the transition metal or transition metal precursor and the $R^1$—O—Y—O—$R^2$ or $R^1$—OC(=O)—Y—C(=O)O$R^2$ backbone structure ligand.

The co-catalyst may be a single compound or a mixture thereof. Examples of the co-catalyst may include organic aluminum compounds, organic boron compounds, organic and inorganic acids, salts, and the like. The organic aluminum compounds may include a compound represented by Chemical Formula $AlR_3$ (where R is each independently a $C_1$-$C_{12}$ alkyl group, an oxygen-containing alkyl group, or a halide) and a compound such as $LiAlH_4$. Examples thereof may include trimethyl aluminum, triethyl aluminum, tri-isobutyl aluminum, tri-n-octyl aluminum, methyl aluminum dichloride, methylaluminum dichloride, ethylaluminum dichloride, dimethylaluminum chloride, diethylaluminum chloride, ethylaluminum sesquichloride, methylaluminum sesquichloride, and aluminoxane. Aluminoxane is well known in the art as a typical oligomer compound that can be produced by mixing an alkylaluminum compound, such as trimethylaluminum, with water. Such an oligomer compound may be a linear compound, a cyclic compound, a cage compound, or a mixture thereof. It is believed that commercially available aluminoxanes are generally mixtures of linear and cyclic compounds. Non-limiting examples thereof may include methylaluminoxane, ethylaluminoxane, isobutylaluminoxane, hexylaluminoxane, octylaluminoxane, decylaluminoxane, or mixtures thereof.

Examples of the organic boron compounds may include boroxine, NaBH4, trimethylboron, triethylboron, dimethylphenylammoniumtetra(phenyl)borate, trityltetra(phenyl)borate, triphenylboron, dimethylphenylammonium tetra(pentafluorophenyl)borate, sodiumtetrakis[(bis-3,5-trifluoromethyl)phenyl]borate, $H+(OEt_2)2$[(bis-3,5-trifluoromethyl)phenyl]borate, trityltetra(pentafluorophenyl)borate and tris(pentafluorophenyl) boron, trimethylammonium tetraphenylborate, triethylammonium tetraphenylborate, tripropylammonium tetraphenylborate, tributylammonium tetraphenylborate, trimethylammonium tetrakis(pentafluorophenyl)borate, triethylammonium tetrakis(pentafluorophenyl)borate, tripropylammonium tetrakis(pentafluorophenyl)borate, tributylammonium tetrakis(pentafluorophenyl)borate, anilinium tetraphenylborate, anilinium tetrakis(pentafluorophenyl)borate, pyridinium tetraphenylborate, pyridiniumtetrakis(pentafluorophenyl)borate, ferrocenium tetrakis(pentafluorophenyl)borate, silver tetraphenylborate, silver tetrakis(pentafluorophenyl)borate, tris(pentafluorophenyl)borane, tris(2,3,5,6-tetrafluorophenyl)borane, tris(2,3,4,5-tetraphenylphenyl)borane, tris(3,4,5-trifluorophenyl)borane, and the like.

These organic boron compounds may be used as mixed with the organic aluminum compounds.

The present disclosure provides a process for producing ethylene oligomers which is a more efficient process for producing α-olefin including a double bond and having 10 to 12 carbon atoms via a novel oligomerization method and a process for producing α-olefin which has an improved selectivity of α-olefin having 10 to 12 carbon atoms and has an improved purity.

The foregoing summary is illustrative only and is not intended to be in any way limiting. In addition to the illustrative aspects, embodiments, and features described above, further aspects, embodiments, and features will become apparent by reference to the drawing and the following detailed description.

[Method for Producing Ethylene Oligomerization]

The present disclosure provides a process for producing α-olefin which has an improved selectivity of α-olefin having 10 to 18 carbon atoms and has an improved purity via a one-stage oligomerization reaction or a two-stage oligomerization reaction.

Specifically, C4" (butenes)-C30" (olefins having 30 carbon atoms) are obtained via a one-stage oligomerization reaction, and among them, C6" (hexenes) or C8" (octenes) are reused to perform a two-stage oligomerization reaction.

In order for the catalyst system described in the present disclosure to express a higher catalytic activity when the ethylene oligomerization is carried out, it is preferable to use an appropriate reaction solvent and use components, i.e., procatalyst, co-catalyst, and other additives, required for the catalyst system, under the selected reaction conditions with a composition ratio in a predetermined range. Herein, oligomerization may be performed in the slurry phase, liquid phase, gas phase, or bulk phase. If the oligomerization is performed in the liquid or slurry phase, a reaction solvent may be used as a medium. As a preferable example of the method for producing an ethylene oligomer, the above-described catalyst (for example, procatalyst, co-catalyst) for ethylene oligomer, ethylene, and a solvent may be added into a reactor to react ethylene in ethylene oligomerization, and, thus, an ethylene oligomer can be produced.

In preparing the catalyst used in the present disclosure, the amount of the co-catalyst is in the range of generally 0.1 to 20,000, preferably 1 to 4,000, aluminum or boron atoms per chromium atom. If the concentration of each component is out of the above-described range, the catalytic activity may become too low or an undesirable side reaction such as the production of polymer may occur. In the catalyst system exemplified in the present disclosure, the transition metal or transition metal precursor, the $R^1$—O—Y—O—$R^2$ or $R^1$—OC(=O)—Y—C(=O)$OR^2$ backbone structure ligand and the co-catalyst are added simultaneously or sequentially in arbitrary order into an arbitrary proper solvent in the presence or absence of a monomer, and, thus, an active catalyst can be obtained. For example, the transition metal precursor, the $R^1$—O—Y—O—$R^2$ or $R^1$—OC(=O)—Y—C(=O)$OR^2$ backbone structure ligand, the co-catalyst, and the monomer may be brought into contact with each other simultaneously, or the transition metal precursor, the $R^1$—O—Y—O—$R^2$ or $R^1$—OC(=O)—Y—C(=O)$OR^2$ backbone structure ligand and the co-catalyst may be added simultaneously or sequentially in arbitrary order and then brought into contact with the monomer, or the transition metal precursor and the $R^1$—O—Y—O—$R^2$ or $R^1$—OC(=O)—Y—C(=O)$OR^2$ backbone structure ligand may be added together to form a metal-ligand complex which can be separated and then added to the co-catalyst so as to be brought into contact with the monomer, or the transition metal precursor, the $R^1$—O—Y—O—$R^2$ or $R^1$—OC(=O)—Y—C(=O)$OR^2$ backbone structure ligand and the co-catalyst may be added together to form a metal-ligand complex which can be separated and then brought into contact with the monomer. Examples of a solvent proper for contact between the components of the catalyst or catalyst system may include hydrocarbon solvents, such as heptane, toluene, 1-hexene, and the like, and polar solvents, such as diethyl ether, tetrahydrofuran, acetonitrile, dichloromethane, chloroform, chlorobenzene, methanol, acetone, and the like, but may not be limited thereto.

The reaction conditions for ethylene oligomerization in the presence of the catalyst exemplified in the present disclosure are not particularly limited. For example, a reaction temperature may be in the range of 0° C. to 200° C. and preferably 20° C. to 100° C. and a reaction pressure may be in the range of 1 bar to 100 bar and preferably 5 bar to 70 bar. The duration of the reaction may vary depending on the activity of the catalyst system, and a reaction time of 5 minutes to 3 hours may be applied. Thus, the reaction can be completed effectively.

The oligomerization of the present disclosure may proceed as a continuous process and may be performed via a one-stage oligomerization reaction or a two-stage oligomerization reaction. As a non-limiting example, an ethylene continuous process according to the process for producing ethylene oligomers of the present disclosure may be performed according to a process including an oligomerization stage and a purification stage as illustrated in FIG. 1.

Firstly, a purification stage of separating ethylene oligomers from a reaction product of the above-described ethylene oligomerization is performed. The purification process is not particularly limited, and components included in the reaction product of the above-described ethylene oligomerization can be separated using a typical separation column and 1-butene, 1-hexene, and 1-octene among the separated oligomers are recycled in an oligomerization reactor. Thus, a method for producing α-olefin which has an improved selectivity of α-olefin having 10 to 12 carbon atoms and has an improved purity as suggested in the present disclosure can be completed. As a more specific example, a feed including a catalyst system 1 as exemplified above, ethylene, recycled dimer (butene), trimer (hexene) and tetramer (octene), and a solvent 2 is continuously introduced into a reaction system illustrated in FIG. 1 and ethylene oligomerization is carried out under the reaction conditions exemplified above. An ethylene oligomerization product which is continuously discharged during the oligomerization is transferred to a gas-liquid separator. Herein, some gas phase compounds are separated and recycled. The unreacted ethylene among the ethylene oligomerization product is collected in a C2" separator 5 and then recycled as a part of the feed. After the separation of ethylene, ethylene oligomers are transferred to a distiller 6 and a dimer (C4"), trimer (C6"), and tetramer (C8") are separated and then recycled in the oligomerization reactor. A polymer 9 of C10" or more is separated and collected and thus can be obtained as an ethylene oligomer according to the present disclosure.

Further, the purification stage may include a process 7 of adding ethylene to ethylene recycled in the oligomerization-product, and may include a process 8 of adding hexene and octene to the recycled dimer (butene), trimer (hexene) and tetramer (octene).

Further aspects and areas of applicability will become apparent from the description provided herein. It should be understood that various aspects of this disclosure may be implemented individually or in combination with one or more other aspects. It should also be understood that the description and specific examples herein are intended for purposes of illustration only and are not intended to limit the scope of the present disclosure.

DRAWING

The drawing described herein is for illustrative purposes only of selected embodiments and not all possible implentations, and is not intended to limit the scope of the present disclosure.

FIG. 1 is a diagram illustrating an ethylene continuous process for a process for producing ethylene oligomers of the present disclosure.

DETAILED DESCRIPTION

Example embodiments will now be described more fully with reference to the accompanying drawing.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, examples of the present disclosure will be described in more detail. However, the following examples are provided to aid in the understanding of the present disclosure, but shall not be construed as limiting the scope of the present disclosure, and various modifications and changes can be made from the following examples without departing from the spirit of the present disclosure.

[Materials and Analysis Instrument]

The synthesis reactions described below were performed under an inert atmosphere such as nitrogen or argon using Standard Schlenk and Glove Box techniques.

Solvents for synthesis such as tetrahydrofuran (THF), normalhexane (n-Hexane), normalpentane (n-Pentane), diethylether and methylene chloride ($CH_2Cl_2$) were passed through an activated alumina column to remove moisture and then used as being preserved on an activated molecular sieve.

Gas chromatography (GC) analysis was performed using an Agilent technologies 7890A GC system under the conditions including a carrier gas of $N_2$, a carrier gas flow of 2.0 mL/min, a split ratio of 20/1, an initial oven temperature of 50° C., an initial time of 2 min, a ramp of 10° C./min, and a final temperature of 280° C. A column used herein was an HP-5, and ethanol or nonane was quantified to be used as internal standard.

EXAMPLES

Diethyl-2,3-diisobutylsuccinate (WO 00/63261) was synthesized by the processes disclosed in the corresponding documents. Methyl aluminoxane, a 10% w/w solution in toluene, was purchased from Albemarle and the other reagents such as triethyl aluminum were purchased from Aldrich chemical company unless otherwise noted.

Catalyst Synthesis Example 1

$CrCl_3(THF)_3$ (0.02 mmol) was introduced into a Schlenk flask, and 40 ml of methylenechloride was added thereto and stirred. Then, diethyl-2,3-diisobutyl-succinate (0.02 mmol) was slowly added thereto, and the solution was stirred for 4 hours. Then, the solvent was removed under reduced pressure and the resultant solid was suspended in toluene and then used as a stock solution.

Catalyst Synthesis Comparative Example 1

Zirconium tetrachloride ($ZrCl_4$) (2.5 mmol) was introduced into a Schlenk flask, and 50 ml of toluene was added thereto with stirring. A triethyl aluminum solution (3.9 mmol) was added thereto for 30 minutes with stirring. Then, an ethylaluminum sesquichloride solution (13.6 mmol) was further added thereto for 30 minutes. Then, the temperature was increased to 70° C. and a reaction was carried out for 1 hour. Then, the temperature was lowered to room temperature, and the entire solution was used as a catalyst stock solution.

Example 1

A 300-ml stainless steel reactor was washed with nitrogen in a vacuum and then 50 ml of toluene was added thereto, and 10.0 mmol-Al MAO was added thereto. Then, the temperature was increased to 65° C. A 0.01 mmol toluene solution was taken out of the catalyst stock solution prepared in Catalyst Synthesis Example 1 and then introduced into the reactor. 50 ml of toluene was introduced into a pressure reactor and ethylene was fed into the pressure reactor under a pressure of 32 bar and then stirred at a stirring speed of 600 rpm. After 30 minutes, the supply of ethylene into the reactor was stopped and the stirring was stopped to stop the reaction. The reactor was cooled to lower than 10° C. After the unreacted ethylene within the reactor was discharged, ethanol mixed with 10 vol % of hydrochloric acid was added to the liquid present in the reactor. A small amount of an organic layer sample was passed through anhydrous magnesium sulfate and dried and then analyzed using GC-FID. The remaining organic layer was filtered to separate a solid wax/polymer product therefrom. The organic layer was separated into C6" (hexene) and C8" (octene) via distillation. After the solid product was dried in an oven at a temperature of 100° C. overnight, a polymer was obtained and the weight of the polymer was checked. The oligomer distribution in the reaction mixture obtained via GC analysis is given in Table 1.

Example 2

The process of Example 1 was performed in the same manner except that 14 ml of 1-hexene was additionally used after 50 ml of toluene was introduced into the reactor, and the result of GC analysis and the oligomer distribution are given in Table 1. In the result of GC analysis, the unreacted part of the added 1-hexene was excluded from the calculation of the oligomer distribution.

Example 3

The process of Example 1 was performed in the same manner except that 35 ml of 1-hexene was additionally used after 50 ml of toluene was introduced into the reactor, and the result of GC analysis and the oligomer distribution are given in Table 1. In the result of GC analysis, the unreacted part of the added 1-hexene was excluded from the calculation of the oligomer distribution.

Example 4

The process of Example 1 was performed in the same manner except that 70 ml of 1-hexene was additionally used after 50 ml of toluene was introduced into the reactor, and the result of GC analysis and the oligomer distribution are given in Table 1. In the result of GC analysis, the unreacted part of the added 1-hexene was excluded from the calculation of the oligomer distribution.

Example 5

The process of Example 1 was performed in the same manner except that 15 ml of 1-octene was additionally used after 50 ml of toluene was introduced into the reactor, and the result of GC analysis and the oligomer distribution are given in Table 1. In the result of GC analysis, the unreacted part of the added 1-octene was excluded from the calculation of the oligomer distribution.

Example 6

The process of Example 1 was performed in the same manner except that 25 ml of 1-octene was additionally used after 50 ml of toluene was introduced into the reactor, and the result of GC analysis and the oligomer distribution are given in Table 1. In the result of GC analysis, the unreacted part of the added 1-octene was excluded from the calculation of the oligomer distribution.

Example 7

The process of Example 1 was performed in the same manner except that 80 ml of 1-octene was additionally used after 50 ml of toluene was introduced into the reactor, and the result of GC analysis and the oligomer distribution are given in Table 1. In the result of GC analysis, the unreacted part of the added 1-octene was excluded from the calculation of the oligomer distribution.

Example 8

The process of Example 1 was performed in the same manner except that 35 ml of 1-hexene and 25 ml of 1-octene were additionally used after 50 ml of toluene was introduced into the reactor, and the result of GC analysis and the oligomer distribution are given in Table 1. In the result of GC analysis, the unreacted part of the added 1-hexene and 1-octene was excluded from the calculation of the oligomer distribution.

Example 9

The process of Example 1 was performed in the same manner except that 35 ml of 1-hexene and 25 ml of 1-octene were additionally used after 50 ml of toluene was introduced into the reactor and oligomerization was carried out at 25° C., and the result of GC analysis and the oligomer distribution are given in Table 1. In the result of GC analysis, the unreacted part of the added 1-hexene and 1-octene was excluded from the calculation of the oligomer distribution.

Comparative Example 1

A 300-ml stainless steel reactor was washed with nitrogen in a vacuum and then 50 ml of toluene was added thereto, and 10.0 mmol-Al MAO was added thereto. Then, the temperature was increased to 65° C.

A 0.3 mmol toluene solution was taken out of the catalyst stock solution prepared in Catalyst Synthesis Example 1 and then introduced into the reactor. Ethylene was fed into a pressure reactor under a pressure of 32 bar and then stirred at a stirring speed of 600 rpm. After 30 minutes, the supply of ethylene into the reactor was stopped and the stirring was stopped to stop the reaction. The reactor was cooled to lower than 10° C. After the unreacted ethylene within the reactor was discharged, ethanol mixed with 10 vol % of hydrochloric acid was added to the liquid present in the reactor. A small amount of an organic layer sample was passed through anhydrous magnesium sulfate and dried and then analyzed using GC-FID. The remaining organic layer was filtered to separate a solid wax/polymer product therefrom. The organic layer was separated into C6" (hexene) and C8" (octene) via distillation. After the solid product was dried in an oven at a temperature of 100° C. overnight, a polymer was obtained and the weight of the polymer was checked. The oligomer distribution in the reaction mixture obtained via GC analysis is given in Table 1.

Comparative Example 2

The process of Example 1 was performed in the same manner except that 15 ml of 1-octene was additionally used after 50 ml of toluene was introduced into the reactor according to Comparative Example 1, and the result of GC analysis and the oligomer distribution are given in Table 1. In the result of GC analysis, the unreacted part of the added 1-octene was excluded from the calculation of the oligomer distribution.

Comparative Example 3

The process of Example 1 was performed in the same manner except that 25 ml of 1-octene was additionally used after 50 ml of toluene was introduced into the reactor according to Comparative Example 1. In the result of GC analysis, the unreacted part of the added 1-octene was excluded from the calculation of the oligomer distribution.

Comparative Example 4

The process of Example 1 was performed in the same manner except that 80 ml of 1-octene was additionally used after 50 ml of toluene was introduced into the reactor according to Comparative Example 1. In the result of GC analysis, the unreacted part of the added 1-octene was excluded from the calculation of the oligomer distribution.

Comparative Example 5

The process of Example 1 was performed in the same manner except that 35 ml of 1-hexene and 25 ml of 1-octene were additionally used after 50 ml of toluene was introduced into the reactor according to Comparative Example 1. In the result of GC analysis, the unreacted part of the added 1-hexene and 1-octene was excluded from the calculation of the oligomer distribution.

TABLE 1

| | | Example 1 | Example 2 | Example 3 | Example 4 | Example 5 | Example 6 | Example 7 | Example 8 |
|---|---|---|---|---|---|---|---|---|---|
| Activity | (Kg-lefins/g-[M]/hr) | 62.5 | 229 | 213 | 176 | 174 | 146 | 140 | 117 |
| Oligomer Distribution and purity | $C_6''$ (wt %) | 18.3 | 11.8 | 5.8 | 5.4 | 6.4 | 6.4 | 7.1 | 7.6 |
| | $C_8''$ (wt %) | 221. | 18.8 | 17.6 | 16.2 | 13.3 | 12.8 | 10.9 | 12.2 |
| | $C_{10}''$-$C_{12}''$ (wt %) | 28.1 | 32.4 | 35.2 | 36.5 | 39.7 | 39 | 41.7 | 50.7 |
| | $C_{12+}''$ (wt %) | 24.4 | 30.7 | 34.7 | 36.3 | 34.8 | 35.8 | 35.3 | 22.3 |
| | $C_{10}''$ Purity $(1-C_{10}''/C_{10}'')$ (wt %) | — | 94.2 | 93.3 | 92.8 | 95.4 | 95.2 | 93.2 | 93.6 |

| | | Example 9 | Comparative Example. 1 | Comparative Example. 2 | Comparative Example. 3 | Comparative Example. 4 | Comparative Example. 5 |
|---|---|---|---|---|---|---|---|
| Activity | (Kg-lefins/g-[M]/hr) | 202 | 6.7 | 23 | 23 | 21 | 23 |
| Oligomer Distribution and purity | $C_6''$ (wt %) | 5.8 | 20.8 | 18.5 | 20.1 | 22.3 | 7.8 |
| | $C_8''$ (wt %) | 12.3 | 10.2 | 5.8 | 5.8 | 4.8 | 4.8 |
| | $C_{10}''$-$C_{12}''$ (wt %) | 57.8 | 17.2 | 29.1 | 27.3 | 23.7 | 38.4 |
| | $C_{12+}''$ (wt %) | 18.3 | 18.4 | 20.2 | 21.8 | 22.6 | 26.6 |
| | $C_{10}''$ Purity $(1-C_{10}''/C_{10}'')$ (wt %) | 96.5 | — | 71.1 | 74.5 | 78.1 | 66.7 |

As listed in Table 1, it can be seen from the results of oligomerization according to Example 2 to Example 9 of the present disclosure carried out by recycling C6'' olefin and $C_8''$ olefin among olefins prepared in Example 1 that in the oligomer distribution, $C_{10}''$ and $C_{12}''$ olefins are highly distributed via the novel oligomerization method of the present disclosure as compared with Comparative Examples 2 to 5. As exhibited in Example 2 to Example 9, the olefins have a very high purity.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

EXPLANATION OF REFERENCE NUMERALS

1: Catalyst
2: Solvent
3: Reactor
4: Catalyst deactivation/Gas-liquid separator
5: $C_2''$ separator
6: Distiller
7: Introduce $C_2''$
8: Introduce $C_6''/C_8''$
9: $C_{10+}''$ olefin The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A process for producing ethylene oligomers, the process comprising:
   introducing a catalyst system and ethylene in a reactor;
   carrying out oligomerization of the ethylene in the reactor to produce a reaction product;
   separating the ethylene oligomers from the reaction product; and
   recycling butene, hexene, and octene from the ethylene oligomers back in the oligomerization reaction,
   wherein the catalyst system comprises a transition metal or transition metal precursor, a ligand with a backbone structure expressed by the following General Formula 1, and a co-catalyst:

$R^1-OC(=O)-Y-C(=O)OR^2$  [General Formula 1]

wherein $R^1$, $R^2$ are each independently hydrocarbyl, substituted hydrocarbyl, heterohydrocarbyl, or substituted heterohydrocarbyl, and Y represents a group connecting $C(=O)O$ and is hydrocarbyl, substituted hydrocarbyl, heterohydrocarbyl, or substituted heterohydrocarbyl.

2. The process for producing ethylene oligomers of claim 1, wherein the ligand with a backbone structure expressed by General Formula 1 is any one selected from dicarboxylic acid ester compounds represented by the following General Formula 2 to General Formula 6:

(2)
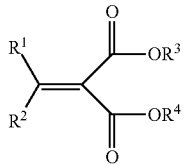

wherein $R^1$ and $R^2$ are each independently hydrogen or a linear or branched alkyl group having 1 to 20 carbon atoms, a cyclic alkyl group or alkenyl group having 3 to 20 carbon atoms, an aryl group having 6 to 20 carbon atoms, or an arylalkyl group or alkylaryl group having 7 to 20 carbon atoms and are combined to form a cycle, and $R^3$ and $R^4$ are each independently a linear or branched alkyl group having 1 to 20 carbon atoms, (3)
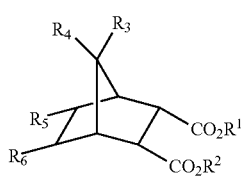

(4)
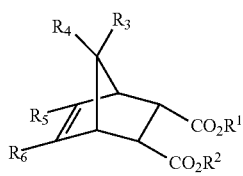

(5)
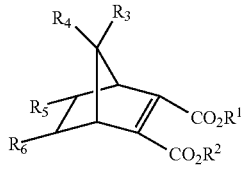

(6)
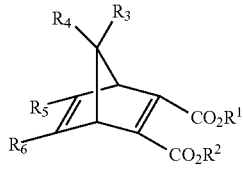

wherein $R^1$ and $R^2$ are identical to or different from each other and represent linear, branched, or cyclic alkyl groups or alkenyl groups having 1 to 20 carbon atoms, aryl groups having 6 to 20 carbon atoms, or arylalkyl groups or alkylaryl groups having 7 to 20 carbon atoms; and $R^3$, $R^4$, $R^5$ and $R^6$ are identical to or different from each other and represent hydrogen, linear, branched, or cyclic alkyl groups or alkenyl groups having 1 to 20 carbon atoms, aryl groups having 6 to 20 carbon atoms, or arylalkyl groups or alkylaryl groups having 7 to 20 carbon atoms.

3. The process for producing ethylene oligomers of claim 2, wherein the dicarboxylic acid ester of General Formula 2 is any one selected from malonate, succinate, glutarate, pivalate, adipate, sebacate, malate, naphthalene dicarboxylate, trimellitate, benzene-1,2,3-tricarboxylate, pyromellitate, and carbonate.

4. The process for producing ethylene oligomers of claim 3, wherein the dicarboxylic acid ester of General Formula 2 is any one selected from diethyl malonate, dibutyl malonate, dimethylsuccinate, diethylsuccinate, dinormalpropyl succinate, diisopropylsuccinate, 1,1-dimethyl-dimethylsuccinate, 1,1-dimethyl-diethylsuccinate, 1,1-dimethyl-dinormalpropylsuccinate, 1,1-dimethyl-diisopropylsuccinate, 1,2-dimethyl-dimethylsuccinate, 1,2-dimethyl-diethylsuccinate, ethyl-dimethylsuccinate, ethyl-diethylsuccinate, ethyl-dinormalpropylsuccinate, ethyl-diisopropylsuccinate, 1,1-diethyl-dimethylsuccinate, 1,1-diethyl-diethylsuccinate, 1,1-diethyl-dimethylsuccinate, 1,2-diethyl-dimethylsuccinate, 1,2-diethyl-diethylsuccinate, 1,2-diethyl-dinormalpropylsuccinate, 1,2-diethyl-diisopropylsuccinate, normalpropyl-dimethylsuccinate, normalpropyl-diethylsuccinate, normalpropyl-dinormalpropylsuccinate, normalpropyl-diisopropylsuccinate, isopropyl-dimethylsuccinate, isopropyl-diethylsuccinate, isopropyl-dinormalpropylsuccinate, isopropyl-diisopropylsuccinate, 1,2-diisopropyl-dimethylsuccinate, 1,2-diisopropyl-diethylsuccinate, 1,2-diisopropyl-dinormalpropylsuccinate, 1,2-diisopropyl-diisopropylsuccinate, normalbutyl-dimethylsuccinate, normalbutyl-diethylsuccinate, normalbutyl-dinormalpropylsuccinate, normalbutyl-diisopropylsuccinate, isobutyl-dimethyl succinate, isobutyl-diethylsuccinate, isobutyl-dinormalpropylsuccinate, isobutyl-diisopropylsuccinate, 1,2-dinormalbutyl-dimethylsuccinate, 1,2-dinormalbutyl-diethylsuccinate, 1,2-dinormalbutyl-dinormalpropylsuccinate, 1,2-dinormalbutyl-diisopropylsuccinate, 1,2-dinormalbutyl-dimethylsuccinate, 1,2-diisobutyl-dimethylsuccinate, 1,2-diisobutyl-diethylsuccinate, 1,2-diisobutyl-dinormalpropylsuccinate, 1,2-diisobutyl-diisopropylsuccinate, diethyl adipate, dibutyl adipate, diethyl sebacate, dibutyl sebacate, diethyl malate, di-n-butyl malate, diethyl naphthalene dicarboxylate, dibutyl naphthalene dicarboxylate, triethyl trimellitate, tributyl trimellitate, triethyl benzene-1,2,3-tricarboxylate, tributyl benzene-1,2,3-tricarboxylate, tetraethyl pyromellitate, and tetrabutyl pyromellitate.

5. The process for producing ethylene oligomers of claim 1, wherein the transition metal or transition metal precursor is chromium or a chromium precursor.

6. The process for producing ethylene oligomers of claim 5, wherein the chromium or chromium precursor is selected from the group consisting of chromium(III)acetylacetonate, chromium trichloride tristetrahydrofuran, and chromium (III)2-ethylhexanoate.

7. The process for producing ethylene oligomers of claim 1, wherein the co-catalyst includes one or more selected from methylaluminoxane (MAO), ethylaluminoxane (EAO), and isobutylaluminoxane (IBAO).

8. The process for producing ethylene oligomers of claim 1, wherein the co-catalyst is a combination of trialkylaluminum and the following borate or boron compound:
dimethylphenylammoniumtetra(phenyl)borate, trityltetra (phenyl)borate, triphenylboron, dimethylphenylammoniumtetra(pentafluorophenyl)borate, sodiumtetrakis [(bis-3,5-trifluoromethyl)phenyl]borate, H+(OEt$_2$)2 [(bis-3,5-trifluoromethyl)phenyl]borate, trityltetra (pentafluorophenyl)borate and tris(pentafluorophenyl) boron, trimethylammonium tetraphenylborate, triethylammonium tetraphenylborate, tripropylammonium tetraphenylborate, tributylammonium tetraphenylborate, trimethylammonium tetrakis(pentafluorophenyl)borate, triethylammonium tetrakis(pentafluorophenyl)borate, tripropylammonium tetrakis(pentafluorophenyl)borate, tributylammonium tetrakis(pentafluorophenyl)borate, anilinium tetraphenylborate, anilinium tetrakis(pentafluorophenyl)borate, pyridinium tetraphenylborate, pyridiniumtetrakis(pentafluorophenyl)borate, ferrocenium tetrakis(pentafluorophenyl)borate, silver tetraphenylborate, silver tetrakis(pentafluorophenyl)borate, tris(pentafluorophenyl)borane, tris(2,3,5,6-tetrafluorophenyl)borane, tris(2,3,4,5-tetraphenylphenyl)borane, and tris(3,4,5-trifluorophenyl)borane.

9. The process for producing ethylene oligomers of claim 2, wherein the transition metal or transition metal precursor is chromium or a chromium precursor.

10. The process for producing ethylene oligomers of claim 2, wherein the co-catalyst includes one or more selected from methylaluminoxane (MAO), ethylaluminoxane (EAO), and isobutylaluminoxane (IBAO).

11. The process for producing ethylene oligomers of claim 2, wherein the co-catalyst is a combination of trialkylaluminum and the following borate or boron compound: dimethylphenylammoniumtetra(phenyl)borate, trityltetra(phenyl)borate, triphenylboron, dimethylphenylammoniumtetra(pentafluorophenyl)borate, sodiumtetrakis[(bis-3,5-trifluoromethyl)phenyl]borate, $H^+(OEt_2)_2$[(bis-3,5-trifluoromethyl)phenyl]borate, trityltetra(pentafluorophenyl)borate and tris(pentafluorophenyl)boron, trimethylammonium tetraphenylborate, triethylammonium tetraphenylborate, tripropylammonium tetraphenylborate, tributylammonium tetraphenylborate, trimethylammonium tetrakis(pentafluorophenyl)borate, triethylammonium tetrakis(pentafluorophenyl)borate, tripropylammonium tetrakis(pentafluorophenyl)borate, tributylammonium tetrakis(pentafluorophenyl)borate, anilinium tetraphenylborate, anilinium tetrakis(pentafluorophenyl)borate, pyridinium tetraphenylborate, pyridiniumtetrakis(pentafluorophenyl)borate, ferrocenium tetrakis(pentafluorophenyl)borate, silver tetraphenylborate, silver tetrakis(pentafluorophenyl)borate, tris(pentafluorophenyl)borane, tris(2,3,5,6-tetrafluorophenyl)borane, tris(2,3,4,5-tetraphenylphenyl)borane, and tris(3,4,5-trifluorophenyl)borane.

* * * * *